US011981634B2

(12) United States Patent
Wendlinger

(10) Patent No.: US 11,981,634 B2
(45) Date of Patent: May 14, 2024

(54) METHOD FOR PREPARING FLUOROORGANIC COMPOUNDS

(71) Applicant: Arkema France, Colombes (FR)

(72) Inventor: Laurent Wendlinger, Soucieu en Jarrest (FR)

(73) Assignee: ARKEMA FRANCE, Colombes (FR)

( * ) Notice: Subject to any disclaimer, the term of this patent is extended or adjusted under 35 U.S.C. 154(b) by 845 days.

(21) Appl. No.: 16/615,708

(22) PCT Filed: May 22, 2018

(86) PCT No.: PCT/EP2018/063316
§ 371 (c)(1),
(2) Date: Nov. 21, 2019

(87) PCT Pub. No.: WO2018/215418
PCT Pub. Date: Nov. 29, 2018

(65) Prior Publication Data
US 2020/0223777 A1    Jul. 16, 2020

(30) Foreign Application Priority Data

May 23, 2017   (FR) ...................................... 1754557

(51) Int. Cl.
*H01M 10/0525* (2010.01)
*C07C 51/363* (2006.01)
*H01M 10/0567* (2010.01)
*H01M 10/0569* (2010.01)

(52) U.S. Cl.
CPC ....... *C07C 51/363* (2013.01); *H01M 10/0525* (2013.01); *H01M 10/0567* (2013.01); *H01M 10/0569* (2013.01); *H01M 2300/0034* (2013.01)

(58) Field of Classification Search
CPC ......... H01M 10/0525; H01M 10/0567; H01M 10/0569; H01M 2300/0034
See application file for complete search history.

(56) References Cited

U.S. PATENT DOCUMENTS

| 5,072,030 | A | 12/1991 | Bielefeldt et al. |
| 2004/0024243 | A1 | 2/2004 | Mathieu et al. |
| 2014/0075746 | A1* | 3/2014 | Schmidt ............ H01M 10/0525 423/385 |
| 2015/0155601 | A1* | 6/2015 | Nakatsutsumi ....... H01M 4/587 429/343 |

FOREIGN PATENT DOCUMENTS

| EP | 0132681 A1 | 2/1985 |
| JP | S5569501 A | 5/1980 |
| WO | 0181353 A1 | 11/2001 |

OTHER PUBLICATIONS

International Search Report (with English Translation) and Written Opinion issued in corresponding International Patent Application No. PCT/EP2018/063316, 15 pages (dated Aug. 2, 2018).
Chuvatkin, N., et al., "Reactions of Chlorine Monofluoride. III. Substitution of Chlorine Atoms by Fluorine in Chlorine-Substituted Alkanes and Esters," Journal of Organic Chemistry USSR, Plenum Publ. Corp, US, vol. 18, No. 5, pp. 821-827 (May 1, 1982).
Chuvatkin, N., et al., "Reactions of Halogen Fluorides. XIII. New Possibilities for Oxidative Nucleophilic Fluorination of Bromine-Substituted Esters by the Hexachloromelamine—Hydrogen Fluoride System," Russian Journal of Organic Chemistry, vol. 29, No. 9.1, pp. 1450-1456 (1993).
Feng, C. et al."3.2.2 Reaction of Substituting Other Halogens (Cl, Br, I) in Organics with Fluorine in a Pentyl Fluoride", Organoelementary Compounds and Polymers Thereof, National Defense Science and Technology University Press, pp. 34-39, English translation only (9 pages), Date Mar. 1999.

* cited by examiner

*Primary Examiner* — Osei K Amponsah
(74) *Attorney, Agent, or Firm* — BUCHANAN, INGERSOLL & ROONEY PC

(57) ABSTRACT

A process for preparing a compound of formula (I) $HR^1R^2C-CF_2-(C=O)-Y$ starting with a compound of formula (II) $R^1R^2C=CX-(C=O)-Y$ or of formula (III) $HR^1R^2C-CX^1X^2-(C=O)-Y$ placed in contact with hydrofluoric acid; $R^1$ and $R^2$ being independently selected from H, F, Cl, Br, I, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; $X^1$ and $X^2$ being independently selected from F, Cl, Br and I on condition that $X^1$ and $X^2$ are not simultaneously F; Y being selected from the group of H, $C_1$-$C_{20}$-alkyl, $C_1$-$C_{20}$-haloalkyl, $C_6$-$C_{20}$-aryl, —OH, —OR, —$NH_2$, —NHR, —$NR_2$, —SR, $C_3$-$C_{20}$-cycloalkyl, $C_3$-$C_{20}$-cycloalkenyl and $C_2$-$C_{20}$-alkenyl; R being independently selected from the group of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl.

13 Claims, No Drawings

METHOD FOR PREPARING FLUOROORGANIC COMPOUNDS

TECHNICAL FIELD

The present invention relates to a process for preparing organofluorine compounds. In particular, the present invention relates to the preparation of difluoro organic compounds comprising a —(C=O)— functional group.

TECHNOLOGICAL BACKGROUND OF THE INVENTION

Difluoro organic compounds find many applications as synthetic intermediates. Compounds of difluoropropionic acid type are notably known as synthetic intermediates in the preparation of fluoroacrylic acid. Specifically, U.S. Pat. No. 5,072,030 describes the preparation of 2,3-difluoropropionic acid by fluorination of acrylic acid in the presence of fluorine $F_2$. EP 0 132 681 describes the preparation of 2,2-difluoropropionic acid by oxidation of 2,2-difluoronitropropane in the presence of an oxidizing agent such as sulfuric acid. A yield of 85% is obtained.

The preparation of potassium 2,2-difluoropropionate from 2-chloro-3,3-difluorobut-1-ene in the presence of potassium permanganate and potassium hydroxide is also known from JP55-69501. The use of potassium permanganate necessitates subsequent treatments which complicate the implementation of an industrial-scale process.

There is a need for a simple and efficient process for producing difluoro organic compounds. There is notably a need for a process for producing organic compounds with a high purity.

SUMMARY OF THE INVENTION

The present invention is directed toward overcoming the drawbacks identified in the prior art. Thus, according to a first aspect, the present invention relates to a process for preparing a compound of formula (I) $HR^1R^2C—CF_2—(C=O)—Y$ comprising the steps of:

a) placing a compound of formula (II) $R^1R^2C=CX^1—(C=O)—Y$ or of formula (III) $HR^1R^2C—CX^1X^2—(C=O)—Y$ in contact with hydrofluoric acid;

$R^1$ and $R^2$ being independently selected from H, F, Cl, Br, I, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl;

$X^1$ and $X^2$ being independently selected from F, Cl, Br and I on condition that $X^1$ and $X^2$ are not simultaneously F;

Y being selected from the group consisting of H, $C_1$-$C_{20}$-alkyl, $C_1$-$C_{20}$-haloalkyl, $C_6$-$C_{20}$-aryl, —OH, —OR, —NH$_2$, —NHR, —NR$_2$, —SR, $C_3$-$C_{20}$-cycloalkyl, $C_3$-$C_{20}$-cycloalkenyl and $C_2$-$C_{20}$-alkenyl;

R being independently selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; and b) recovery of a stream A comprising said compound (I).

Step a) of the present process allows the formation of a stream A comprising said compound (I). This compound is recovered in step b).

According to a preferred embodiment, Y is —OH or —OR.

According to a preferred embodiment, $R^1$ is H and $R^2$ is H.

According to a preferred embodiment, the process is performed in the presence of a catalyst.

According to a particular embodiment, the process comprises the steps of:

a1) placing the compound of formula (II) $R^1R^2C=CX^1—(C=O)—Y$ or of formula (III) $HR^1R^2C—CX^1X^2—(C=O)—Y$ in contact with hydrofluoric acid under conditions that are effective for forming a compound of formula (IV) $HR^1R^2C—CX^1F—(C=O)—Y$ or of formula (V) $R^1R^2C=CF—(C=O)—Y$ with $R^1$, $R^2$, Y being as defined above and $X^1$ is Cl, Br and I; and a2) placing said compound of formula (IV) $HR^1R^2C—CX^1F—(C=O)—Y$ or of formula (V) $R^1R^2C=CF—(C=O)—Y$ obtained in step a1) in contact with hydrofluoric acid under conditions that are effective for forming said stream A comprising said compound of formula (I) $HR^1R^2C—CF_2—(C=O)—Y$; and b) recovery of said stream A comprising said compound (I).

According to a preferred embodiment, composition A obtained in step a2) comprises less than 15% by weight of compound of formula (IV) $HR^1R^2C—CX^1F—(C=O)—Y$ or of formula (V) $R^1R^2C=CF—(C=O)—Y$ on the basis of the total weight of the compounds of formula (I), (IV) or (IV); advantageously less than 10% by weight on the basis of the total weight of the compounds of formula (I), (IV) or (IV).

According to a preferred embodiment, said stream A is purified under conditions that are effective for forming a composition B comprising a compound of formula (I) $HR^1R^2C—CF_2—(C=O)—Y$, less than 1000 ppm of a compound of formula (IV) $HR^1R^2C—CX^1F—(C=O)—Y$ or of formula (V) $R^1R^2C=CF—(C=O)—Y$ and optionally or not less than 500 ppm of water and optionally or not less than 500 ppm of hydrofluoric acid and optionally or not less than 100 ppm of a hydrogen halide other than hydrofluoric acid, preferably hydrogen chloride.

According to a preferred embodiment, in the compounds of formula (I), (II), (III) and optionally (IV) and (V), Y is —OH; and the compound of formula (I) in which Y is —OH is treated under conditions that are effective for forming a compound of formula (I) in which Y is —OR, R being selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl.

According to a preferred embodiment, R is a $C_1$-$C_6$-alkyl; preferably, R is —CH$_3$, —CH$_2$CH$_3$ or —CH$_2$CH$_2$CH$_3$.

According to another aspect, the present invention relates to a composition B comprising a compound of formula (I) $HR^1R^2C—CF_2—(C=O)—Y$ as defined above, and less than 1000 ppm of a compound of formula (IV) $HR^1R^2C—CX^1F—(C=O)—Y$ or of formula (V) $R^1R^2C=CF—(C=O)—Y$ and optionally or not less than 500 ppm of water and optionally or not less than 500 ppm of hydrofluoric acid and optionally or not less than 100 ppm of a hydrogen halide other than hydrofluoric acid, preferably hydrogen chloride; with $R^1$ and $R^2$ being independently selected from H, F, Cl, Br, I, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; preferably, $R^1$ and $R^2$=H;

$X^1$ being selected from Cl, Br and I; preferably, $X^1$ is Cl;

Y being selected from the group consisting of H, $C_1$-$C_{20}$-alkyl, $C_1$-$C_{20}$-haloalkyl, $C_6$-$C_{20}$-aryl, —OH, —OR, —NH$_2$, —NHR, —NR$_2$, —SR, $C_3$-$C_{20}$-cycloalkyl, $C_3$-$C_{20}$-cycloalkenyl and $C_2$-$C_{20}$-alkenyl; preferably, Y is —OH or —OR;

R being independently selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; preferably, R is $C_1$-$C_6$-alkyl, in particular R is —$CH_3$, —$CH_2CH_3$ or —$CH_2CH_2CH_3$.

According to another aspect of the present invention, the composition is used as solvent in an electrolytic composition in a battery, preferably a lithium-ion battery.

DETAILED DESCRIPTION OF THE INVENTION

The present invention is directed toward overcoming the drawbacks identified in the prior art. Thus, according to a first aspect, the present invention relates to a process for preparing a compound of formula (I) $HR^1R^2C$—$CF_2$—(C=O)—Y starting with a compound of formula (II) $R^1R^2C$=$CX^1$—(C=O)—Y or of formula (III) $HR^1R^2C$—$CX^1X^2$—(C=O)—Y placed in contact with hydrofluoric acid.

In the compounds of formula (I), (II) and/or (III):
- $R^1$ and $R^2$ are independently selected from H, F, Cl, Br, I, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl;
- $X^1$ and $X^2$ are independently selected from F, Cl, Br and I on condition that $X^1$ and $X^2$ are not simultaneously F;
- Y is selected from the group consisting of H, $C_1$-$C_{20}$-alkyl, $C_1$-$C_{20}$-haloalkyl, $C_6$-$C_{20}$-aryl, —OH, —OR, —$NH_2$, —NHR, —$NR_2$, —SR, $C_3$-$C_{20}$-cycloalkyl, $C_3$-$C_{20}$-cycloalkenyl and $C_2$-$C_2$-alkenyl;
- R is independently selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl.

The term "alkyl" refers to linear or branched hydrocarbon-based chains containing the specified number of carbon atoms. For example, $C_1$-$C_6$ alkyl means a linear or branched alkyl group containing at least 1 and not more than 6 carbon atoms. The term "aryl" refers to an aromatic hydrocarbon-based ring containing the specified number of carbon atoms. For example, aryl may be a phenyl, naphthyl, anthracenyl or phenanthryl. The term "cycloalkyl" refers to a monocyclic or fused polycyclic non-aromatic hydrocarbon-based ring including the specified number of carbon atoms. For example, cycloalkyl comprises cyclopropyl, cyclobutyl, cyclopentyl, cyclohexyl, cycloheptyl or cyclooctyl. The term "alkenyl" refers to linear or branched hydrocarbon-based chains containing the specified number of carbon atoms and at least one carbon-carbon double bond. The term "cycloalkenyl" refers to a monocyclic or fused polycyclic non-aromatic hydrocarbon-based ring including the specified number of carbon atoms and at least one carbon-carbon double bond.

Preferably, in the compounds of formula (I), (II) and/or (III), $R^1$ and $R^2$ are independently selected from H, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl. In particular, in the compounds of formula (I), (II) and/or (III), $R^1$ and $R^2$ are independently selected from H, $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl. Preferably, in the compounds of formula (I), (II) and/or (III), $R^1$ and $R^2$ are independently selected from H, $C_1$-$C_3$-alkyl, $C_6$-$C_8$-aryl and $C_2$-$C_6$-alkenyl, $C_3$-$C_6$-cycloalkenyl and $C_3$-$C_6$-cycloalkyl.

Particularly favorably, in the compounds of formula (I), (II) and/or (III), $R^1$ and $R^2$ are H.

Preferably, in the compounds of formula (I), (II) and/or (III), $X^1$ and $X^2$ are independently selected from F, Cl and Br on condition that $X^1$ and $X^2$ are not simultaneously F. More preferentially, in the compounds of formula (I), (II) and/or (III), $X^1$ and $X^2$ are independently selected from F and Cl on condition that $X^1$ and $X^2$ are not simultaneously F. In particular, in the compounds of formula (I), (II) and/or (III), $X^1$ and $X^2$ are Cl.

Preferably, in the compounds of formula (I), (II) and/or (III), Y is selected from the group consisting of H, $C_1$-$C_{10}$-alkyl, $C_1$-$C_{10}$-haloalkyl, $C_6$-$C_{10}$-aryl, —OH, —OR, —$NH_2$, —NHR, —$NR_2$, —SR, $C_3$-$C_{10}$-cycloalkyl, $C_3$-$C_{10}$-cycloalkenyl and $C_2$-$C_{10}$-alkenyl. More preferentially, in the compounds of formula (I), (II) and/or (III), Y is selected from the group consisting of H, $C_1$-$C_{10}$-alkyl, $C_1$-$C_{10}$-haloalkyl, $C_6$-$C_{10}$-aryl, —OH, —OR, $C_3$-$C_{10}$-cycloalkyl, $C_3$-$C_{10}$-cycloalkenyl and $C_2$-$C_{10}$-alkenyl. In particular, in the compounds of formula (I), (II) and/or (III), Y is selected from the group consisting of H, —OH and —OR. More particularly, in the compounds of formula (I), (II) and/or (III), Y is selected from the group consisting of —OH and —OR.

Preferably, R is independently selected from the group consisting of $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl. In particular, R is independently selected from the group consisting of $C_1$-$C_{10}$-alkyl and $C_6$-$C_{10}$-aryl. More particularly, R is independently selected from the group consisting of $C_1$-$C_6$-alkyl and $C_6$-$C_8$-aryl. Favorably, R is independently selected from the group consisting of $C_1$-$C_3$-alkyl and $C_6$-aryl.

Thus, the present invention relates to a process for preparing a compound of formula (I) $HR^1R^2C$—$CF_2$—(C=O)—Y starting with a compound of formula (II) $R^1R^2C$=$CX^1$—(C=O)—Y or of formula (III) $HR^1R^2C$—$CX^1X^2$—(C=O)—Y placed in contact with hydrofluoric acid;
- $R^1$ and $R^2$ being independently selected from H, F, Cl, Br, I, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; preferably selected from H, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; in particular selected from H, $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl; favorably selected from H, $C_1$-$C_3$-alkyl, $C_6$-$C_8$-aryl and $C_2$-$C_6$-alkenyl, $C_3$-$C_6$-cycloalkenyl and $C_3$-$C_6$-cycloalkyl; particularly favorably, $R^1$ and $R^2$ are H;
- $X^1$ and $X^2$ being independently selected from F, Cl, Br and I on condition that $X^1$ and $X^2$ are not simultaneously F; preferably selected from F, Cl and Br on condition that $X^1$ and $X^2$ are not simultaneously F; more preferentially selected from F and Cl on condition that $X^1$ and $X^2$ are not simultaneously F; in particular, $X^1$ and $X^2$ are Cl;
- Y being selected from the group consisting of H, $C_1$-$C_{20}$-alkyl, $C_1$-$C_{20}$-haloalkyl, $C_6$-$C_{20}$-aryl, —OH, —OR, —$NH_2$, —NHR, —$NR_2$, —SR, $C_3$-$C_{20}$-cycloalkyl, $C_3$-$C_{20}$-cycloalkenyl and $C_2$-$C_{20}$-alkenyl; preferably selected from the group consisting of H, $C_1$-$C_{10}$-alkyl, $C_1$-$C_{10}$-haloalkyl, $C_6$-$C_{10}$-aryl, —OH, —OR, —$NH_2$, —NHR, —$NR_2$, —SR, $C_3$-$C_{10}$-cycloalkyl, $C_3$-$C_{10}$-cycloalkenyl and $C_2$-$C_{10}$-alkenyl; more preferentially selected from the group consisting of H, $C_1$-$C_{10}$-alkyl, $C_1$-$C_{10}$-haloalkyl, $C_6$-$C_{10}$-aryl, —OH, —OR, $C_3$-$C_{10}$-cycloalkyl, $C_3$-$C_{10}$-cycloalkenyl and $C_2$-$C_{10}$-alkenyl; in particular selected from the group consisting of H, —OH and —OR; more particularly, Y is selected from the group consisting of —OH and —OR;
- R being independently selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; preferably selected from the group consisting of $C_1$-$C_{10}$- alkyl, $C_6$-$C_{10}$-aryl and $C_2$-$C_{10}$-alkenyl, $C_3$-$C_{10}$-cycloalkenyl and $C_3$-$C_{10}$-cycloalkyl; in particular selected from the group consisting of $C_1$-$C_{10}$-alkyl and $C_6$-$C_{10}$-aryl; more particularly selected from the group consisting of $C_1$-$C_6$-alkyl and $C_6$-$C_8$-aryl; favorably, R is independently selected from the group consisting of $C_1$-$C_3$-alkyl and $C_6$-aryl.

In particular, the present invention relates to a process for preparing a compound of formula (I) $HR^1R^2C—CF_2—(C═O)—Y$ starting with a compound of formula (II) $R^1R^2C═CX^1—(C═O)—Y$ or of formula (III) $HR^1R^2C—CX^1X^2—(C═O)—Y$ placed in contact with hydrofluoric acid;

$R^1$ and $R^2$ being H; $X^1$ and $X^2$ being Cl; Y being selected from the group consisting of —OH and —OR; R being independently selected from the group consisting of $C_1$-$C_3$-alkyl and $C_6$-aryl.

According to a preferred embodiment, the process, i.e. step a), a1) and/or a2), is performed in the presence of a catalyst. Said catalyst may be based on an element or elements selected from metals and/or metalloids from columns 1 to 15 of the Periodic Table of the Elements, and mixtures thereof. Use may be made of a Lewis acid, a catalyst based on a metal halide, notably based on an antimony, tin, tantalum or titanium halide, transition metal halides such as iron, niobium or molybdenum halides, transition metal oxides, halides of metals from group 4, halides of metals from group 5, a fluorinated chromium halide, a fluorinated chromium oxide or a mixture of the two. Metal chlorides and fluorides may advantageously be used. Examples of such catalysts include: $SbCl_5$, $SbCl_3$, $TiCl_4$, $SnCl_4$, $TaCl_5$, $NbCl_5$, $TiCl_4$, $FeCl_3$, $MoCl_6$ and the corresponding fluorinated derivatives thereof. Pentavalent metal halides are suitable for use.

Advantageously, the catalyst is based on an element or elements selected from metals and/or metalloids from columns 4 to 6 and 13 to 15 of the Periodic Table of the Elements, and mixtures thereof. Preferably, said catalyst is based on an element or elements selected from the group consisting of titanium, tantalum, molybdenum, boron, tin and antimony, and mixtures thereof. More preferentially, the catalyst is a halide of an element or elements selected from the group consisting of titanium, tantalum, molybdenum, boron, tin and antimony, and mixtures thereof. In particular, the catalyst is a fluoride, a chloride or a chlorofluoride of an element or elements selected from the group consisting of titanium, tantalum, molybdenum, boron, tin and antimony, and mixtures thereof.

More particularly, said catalyst is based on a metal or metals selected from the group consisting of titanium and tin, or a mixture thereof. Favorably, said catalyst is a halide of a metal or metals selected from the group consisting of titanium and tin, or a mixture thereof. Preferentially favorably, said catalyst is a fluoride, a chloride or a chlorofluoride of a metal or metals selected from the group consisting of titanium and tin, or a mixture thereof.

According to a particularly favored embodiment, the catalyst is selected from antimony trichloride, antimony pentachloride, titanium tetrachloride and tin tetrachloride, and mixtures thereof.

Alternatively, use will be made of a catalyst based on ionic liquid. These ionic liquids are particularly advantageous for liquid-phase fluorination with HF. The term "ionic liquids" refers to nonaqueous salts of ionic nature which are liquid at moderate temperatures (preferably below 120° C.). Ionic liquids preferably result from the reaction between an organic salt and an inorganic compound. Ionic liquids are preferably obtained by reaction of at least one halogen or oxyhalogen-based Lewis acid based on aluminum, titanium, niobium, tantalum, tin, antimony, nickel, zinc or iron with a salt of general formula $Y^+A''$, in which $A''$ denotes a halide anion (bromide, iodide and, preferably, chloride or fluoride) or hexafluoroantimonate ($SbF_6^-$) and $Y^+$ a quaternary ammonium, quaternary phosphonium or ternary sulfonium cation. The halogen Lewis acid based on aluminum, titanium, niobium, tantalum, antimony, nickel, zinc or iron may be a chloro, bromo, fluoro or mixed derivative, for example a chlorofluoro acid. Mention may be made more particularly of the chlorides, fluorides or chlorofluorides having the following formulae:

$TiCl_xFy$ with $x+y=4$ and $0≤x≤4$ $TiCl_xFy$ with $x+y=5$ and $0≤x≤5$ $NbCl_xFy$ with $x+y=5$ and $0≤x≤5$ $SnCl_xFy$ with $x+y=4$ and $1<x<4$ $SbCl_xFy$ with $x+y=5$ and $0≤x≤5$ $AlCl_xFy$ with $x+y=3$ and $0≤x≤3$ $NiCl_xFy$ with $x+y=2$ and $0≤x≤2$ $FeCl_xFy$ with $x+y=3$ and $0≤x≤3$ As examples of such compounds, mention may be made of the following compounds: $TiCl_4$, $TiF_4$, $TaCl_5$, $TaF_5$, $NbCl_5$, $NbF_5$, $SbCl_5$, $SbCl_4F$, $SbCl_3F_2$, $SbCl_2F_3$, $SbClF_4$, $SbF_5$ and mixtures thereof. The following compounds are preferentially used: $TiCl_4$, $TaCl_5+TaF_5$, $NbCl_5+NbF_5$, $SbCl_5$, $SbFCl_4$, $SbF_2Cl_3$, $SbF_3Cl$, $SbF_4Cl$, $SbF_5$ and $SbCl_5+SbF_5$. The antimony-based compounds are more particularly preferred. As examples of oxyhalogen-based Lewis acids that may be used according to the invention, mention may be made of $TiOCl$, $TiOF_2$ and $SbOCl_xFy$ ($x+y=3$). In the salt $Y^+A''$, the cation $Y+$ may correspond to one of the following general formulae:

$R^1R^2R^3R^4N^+$ $R^1R^2R^3R^4P^+$ $R^1R^2R^3S^+$ in which the symbols $R^1$ to $R^4$, which may be identical or different, each denote a saturated or unsaturated, cyclic or non-cyclic, or aromatic hydrocarbyl, chlorohydrocarbyl, fluorohydrocarbyl, chlorofluorohydrocarbyl or fluorocarbyl group containing from 1 to 10 carbon atoms, one or more of these groups also possibly containing one or more heteroatoms such as N, P, S or O. The ammonium, phosphonium or sulfonium cation $Y^+$ may also form part of a saturated or unsaturated, or aromatic heterocycle containing from 1 to 3 nitrogen, phosphorus or sulfur atoms, and may correspond to one or other of the following general formulae:

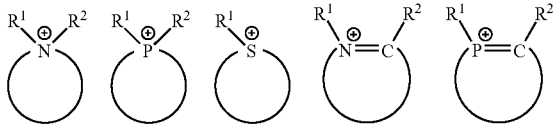

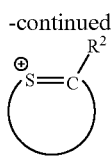

in which R¹ and R² are as defined previously. A salt containing two or three ammonium, phosphonium or sulfonium sites in its formula may also be suitable for use. As examples of salts Y⁺A", mention may be made of tetraalkylammonium chlorides and fluorides, tetraalkylphosphonium chlorides and fluorides, and trialkylsulfonium chlorides and fluorides, alkylpyridinium chlorides and fluorides, dialkylimidazolium chlorides, fluorides and bromides, and trialkylimidazolium chlorides and fluorides. Trimethylsulfonium fluoride or chloride, N-ethylpyridinium chloride or fluoride, N-butylpyridinium chloride or fluoride, 1-ethyl-3-methyl-imidazolium chloride or fluoride, and 1-butyl-3-methylimidazolium chloride or fluoride are more particularly valued. The ionic liquids may be prepared by mixing in an appropriate manner the halogen or oxyhalogen-based Lewis acid and the organic salt Y⁺A". Reference may be made notably to the method described in WO 01/81353. The ionic liquids that are advantageously preferred are those derived from a Lewis acid/organic salt mole ratio strictly greater than 1:1. Mention may also be made of the ionic liquids described in the reference "Liquid-Phase HF Fluorination", Multiphase Homogeneous Catalysis, Eds Wiley-VCH, (2002), 535.

Preferably, the process is performed in the liquid phase.

Preferably, the process is performed continuously or batchwise.

Preferably, said stream A recovered in step b) is a gaseous stream. Besides said compound of formula (I) as defined in the present patent application, the stream A may comprise unreacted hydrofluoric acid, hydrogen halide, and the unreacted compound of formula (II) or of formula (III). The hydrogen halide may be HCl, HBr or HI depending on the substituents X¹ and X² of the compounds of formula (II) or (III).

Preferably, said stream A may comprise less than 15% by weight of hydrofluoric acid, more preferentially less than 10% by weight of hydrofluoric acid on the basis of the total weight of composition A.

Preferably, said stream A may comprise less than 10% by weight of hydrogen halide, preferably hydrogen chloride, more preferentially less than 5% by weight on the basis of the total weight of composition A.

Preferably, said stream A may comprise less than 10% by weight of water, more preferentially less than 5% by weight of water on the basis of the total weight of composition A.

Preferably, said stream A may comprise less than 40% by weight of compounds of formula (II) or (III), more preferentially less than 30% by weight, in particular less than 20% by weight, more particularly less than 10% by weight on the basis of the total weight of composition A.

The process may be performed in the presence or absence of solvent. If a solvent is present, it may be selected from the group consisting of 1,2-dichloroethane, 1,2,3-trichloropropane, 1-chloro-1-fluoroethane, 1,1-difluoroethane, 1,1-dichloroethane, 1,3-dichloro-1-fluorobutane, tetrachlorofluoropropane isomers, trichlorodifluoropropane isomers, dichlorotrifluoropropane isomers, 1,1,1,3,3-pentafluorobutane, 1,1,2-trichloro-2,2-difluoroethane, 1,1,2-trichloro-2-fluoroethane or perchloroethylene, nitro solvents including nitromethane and nitrobenzene, amides, esters, sulfones including tetramethylene sulfone or dimethyl sulfone, or mixtures thereof.

In the present process, the HF/compound of formula (II) or (III) mole ratio is greater than or equal to 2, preferably greater than or equal to 3, in particular greater than or equal to 10.

If a catalyst is used to perform the present process, the catalyst/compound of formula (II) or (III) mole ratio is greater than or equal to 0.01, preferably greater than or equal to 0.025, in particular greater than or equal to 0.05. Alternatively, if a catalyst is used to perform the present process, the catalyst/compound of formula (II) or (III) mole ratio is from 2 to 90 mol %, advantageously from 4 to 80 mol %, preferably from 6 to 75 mol %.

The present process is performed at a temperature of at least 30° C., advantageously of at least 40° C., preferably of at least 50° C., in particular of at least 100° C. Advantageously, the present process is performed at a temperature of from 30° C. to 200° C., preferably from 40° C. to 170° C., in particular from 50° C. to 150° C.

The present process is performed at a pressure of at least 1 bara, advantageously of at least 2 bara, preferably of at least 4 bara, in particular of at least 5 bara. Advantageously, the present process is performed at a pressure of from 1 bara to 50 bara, preferably from 2 bara to 50 bara, more preferentially from 4 bara to 35 bara, in particular from 5 bara to 25 bara.

According to a preferred embodiment, the stream A comprising said compound (I) obtained in step b) may undergo at least one separation and/or purification step, to form a composition B. Separations that may be mentioned include condensation, evaporation, decantation, absorption, washing and liquid-liquid extraction. Purifications that may be mentioned include distillation, for example extractive distillation, azeotropic distillation, membrane separation, adsorption on a solid and more particularly adsorption on molecular sieves, alumina or active charcoal and drying. Preferably, the drying may be performed on molecular sieves, in particular on 3 to 4 Å molecular sieves.

Composition B comprises said compound of formula (I) as described above.

Advantageously, composition B comprises less than 500 ppm of water by weight on the basis of the total weight of composition B, advantageously less than 400 ppm of water, preferably less than 300 ppm of water, in particular less than 200 ppm of water by weight on the basis of the total weight of composition B.

Advantageously, composition B comprises less than 500 ppm of hydrofluoric acid by weight on the basis of the total weight of composition B, advantageously less than 400 ppm of hydrofluoric acid, preferably less than 300 ppm of hydrofluoric acid, more preferentially less than 200 ppm of hydrofluoric acid, in particular less than 100 ppm of hydrofluoric acid by weight on the basis of the total weight of composition B.

Advantageously, composition B comprises less than 100 ppm of a hydrogen halide other than hydrofluoric acid, preferably hydrogen chloride, by weight on the basis of the total weight of composition B, advantageously less than 75 ppm of a hydrogen halide other than hydrofluoric acid, preferably hydrogen chloride, preferably less than 50 ppm of a hydrogen halide other than hydrofluoric acid, preferably hydrogen chloride, in particular less than 20 ppm of a hydrogen halide other than hydrofluoric acid, preferably hydrogen chloride, by weight on the basis of the total weight of composition B.

Said composition B may also comprise less than 1000 ppm by weight of a compound of formula (II) $R^1R^2C=CX^1-(C=O)-Y$ or of formula (III) $HR^1R^2C-CX^1X^2-(C=O)-Y$ as described above, advantageously less than 800 ppm by weight, preferably less than 500 ppm by weight, in particular less than 100 ppm by weight of a compound of formula (II) $R^1R^2C=CX^1-(C=O)-Y$ or of formula (III) $HR^1R^2C-CX^1X^2-(C=O)-Y$ as described above on the basis of the total weight of composition B.

Preferably, besides the compound of formula (I), composition B may comprise:
- optionally or not less than 1000 ppm by weight of a compound of formula (II) $R^1R^2C=CX^1-(C=O)-Y$ or of formula (III) $HR^1R^2C-CX^1X^2-(C=O)-Y$ as described above, advantageously less than 800 ppm by weight, preferably less than 500 ppm by weight, in particular less than 100 ppm by weight of a compound of formula (II) $R^1R^2C=CX^1-(C=O)-Y$ or of formula (III) $HR^1R^2C-CX^1X^2-(C=O)-Y$ as described above; and
- optionally or not less than 500 ppm of water by weight, advantageously less than 400 ppm of water, preferably less than 300 ppm of water, in particular less than 200 ppm of water by weight; and
- optionally or not less than 500 ppm of hydrofluoric acid by weight, advantageously less than 400 ppm of hydrofluoric acid, preferably less than 300 ppm of hydrofluoric acid, more preferentially less than 200 ppm of hydrofluoric acid, in particular less than 100 ppm of hydrofluoric acid by weight; and
- optionally or not less than 100 ppm of a hydrogen halide other than hydrofluoric acid, preferably hydrogen chloride, advantageously less than 75 ppm of a hydrogen halide other than hydrofluoric acid, preferably hydrogen chloride, preferably less than 50 ppm of a hydrogen halide other than hydrofluoric acid, preferably hydrogen chloride, in particular less than 20 ppm of a hydrogen halide other than hydrofluoric acid, preferably hydrogen chloride, by weight on the basis of the total weight of composition B.

According to a preferred embodiment, the present process comprises the steps of:
- a1) placing the compound of formula (II) $R^1R^2C=CX^1-(C=O)-Y$ or of formula (III) $HR^1R^2C-CX^1X^2-(C=O)-Y$ in contact with hydrofluoric acid under conditions that are effective for forming a compound of formula (IV) $HR^1R^2C-CX^1F-(C=O)-Y$ or of formula (V) $R^1R^2C=CF-(C=O)-Y$ with $R^1$, $R^2$, Y being as defined above and $X^1$ is Cl, Br and I; and
- a2) placing said compound of formula (IV) $HR^1R^2C-CX^1F-(C=O)-Y$ or of formula (V) $R^1R^2C=CF-(C=O)-Y$ obtained in step a1) in contact with hydrofluoric acid under conditions that are effective for forming a stream A comprising said compound of formula (I) $HR^1R^2C-CF_2-(C=O)-Y$;
- b) recovery of said stream A comprising said compound (I).

Preferably, said stream A is purified by distillation and/or a drying step as mentioned above.

Preferably, said stream A may comprise less than 15% by weight of hydrofluoric acid, more preferentially less than 10% by weight of hydrofluoric acid on the basis of the total weight of composition A.

Preferably, said stream A may comprise less than 10% by weight of hydrogen halide, preferably hydrogen chloride, more preferentially less than 5% by weight on the basis of the total weight of composition A.

Preferably, said stream A may comprise less than 10% by weight of water, more preferentially less than 5% by weight of water on the basis of the total weight of composition A.

Preferably, said stream A may comprise less than 40% by weight of compounds of formula (II) or (III), more preferentially less than 30% by weight, in particular less than 20% by weight on the basis of the total weight of composition A.

Preferably, composition A obtained in step ii) comprises less than 30% by weight of compounds of formula (IV) $HR^1R^2C-CX^1F-(C=O)-Y$ or of formula (V) $R^1R^2C=CF-(C=O)-Y$ on the basis of the total weight of the compounds of formula (I), (IV) or (IV); advantageously less than 25% by weight of compounds of formula (IV) or (V); preferably less than 20% of compounds of formula (IV) or (V); preferably less than 15% by weight of compounds of formula (IV) or (V); in particular less than 10% by weight of compounds of formula (IV) or (V) on the basis of the total weight of the compounds of formula (I), (IV) or (IV).

Steps i) and ii) may be performed simultaneously or sequentially. Steps i) and ii) may be performed in one reactor or in two different reactors. In step i), the HF/compound of formula (II) or (III) mole ratio may be greater than or equal to 1, advantageously greater than or equal to 2, preferably greater than or equal to 3, in particular greater than or equal to 10.

If a catalyst is used to perform step i), the catalyst/compound of formula (II) or (III) mole ratio is greater than or equal to 0.01, preferably greater than or equal to 0.025, in particular greater than or equal to 0.05. Alternatively, if a catalyst is used to perform the present process, the catalyst/compound of formula (II) or (III) mole ratio is from 2 to 90 mol %, advantageously from 4 to 80 mol %, preferably from 6 to 75 mol %. Preferably, the catalyst may be based on a metal or metals selected from the group consisting of titanium and tin or a mixture thereof; favorably, said catalyst may be a halide of a metal or metals selected from the group consisting of titanium and tin or a mixture thereof; in a preferentially favored manner, said catalyst may be a fluoride, a chloride or a chlorofluoride of a metal or metals selected from the group consisting of titanium and tin or a mixture thereof. In particular, if a catalyst is used to perform step i), said catalyst is tin tetrachloride, antimony pentachloride, antimony trichloride or titanium tetrachloride, or mixtures thereof.

Step i) may be performed at a temperature of at least 30° C., advantageously of at least 40° C., preferably of at least 50° C., in particular of at least 100° C. Advantageously, step i) may be performed at a temperature of from 30° C. to 200° C., preferably from 40° C. to 170° C., in particular from 50° C. to 150° C.

Step i) may be performed at a pressure of at least 1 bara, advantageously of at least 2 bara, preferably of at least 4 bara, in particular of at least 5 bara. Advantageously, step i) may be performed at a pressure of from 1 bara to 50 bara, preferably from 2 bara to 50 bara, more preferentially from 4 bara to 35 bara, in particular from 5 bara to 25 bara.

In step ii), the HF/compound of formula (IV) or (V) mole ratio may be greater than or equal to 1, advantageously greater than or equal to 2, preferably greater than or equal to 3, in particular greater than or equal to 10.

If a catalyst is used to perform step ii), the catalyst/compound of formula (IV) or (V) mole ratio is greater than or equal to 0.01, preferably greater than or equal to 0.025, in particular greater than or equal to 0.05. Alternatively, if a catalyst is used to perform the present process, the catalyst/compound of formula (IV) or (V) mole ratio is from 2 to 90 mol %, advantageously from 4 to 80 mol %, preferably from 6 to 75 mol %. Preferably, the catalyst may be based on a metal or metals selected from the group consisting of titanium and tin or a mixture thereof; favorably, said catalyst may be a halide of a metal or metals selected from the group consisting of titanium and tin or a mixture thereof; in a preferentially favored manner, said catalyst may be a fluoride, a chloride or a chlorofluoride of a metal or metals selected from the group consisting of titanium and tin or a mixture thereof. In particular, if a catalyst is used to perform step ii), said catalyst is antimony pentachloride, antimony trichloride, tin tetrachloride or titanium tetrachloride, or mixtures thereof.

Step ii) may be performed at a temperature of at least 30° C., advantageously of at least 40° C., preferably of at least 50° C., in particular of at least 100° C. Advantageously, step ii) may be performed at a temperature of from 30° C. to 300° C., preferably from 40° C. to 250° C., in particular from 50° C. to 200° C. The temperature in step ii) may be equal to, greater than or less than that of step i). Preferably, the temperature in step ii) is greater than that of step i).

Step ii) may be performed at a pressure of at least 1 bara, advantageously of at least 2 bara, preferably of at least 4 bara, in particular of at least 5 bara. Advantageously, step ii) may be performed at a pressure of from 1 bara to 50 bara, preferably from 2 bara to 50 bara, more preferentially from 4 bara to 35 bara, in particular from 5 bara to 25 bara. The pressure in step ii) may be equal to, greater than or less than that of step i).

Advantageously, the present process comprises the steps of:
- a1) placing the compound of formula (II) $R^1R^2C=CX^1$—$(C=O)$—Y or of formula (III) $HR^1R^2C$—$CX^1X^2$—$(C=O)$—Y in contact with hydrofluoric acid under conditions that are effective for forming a compound of formula (IV) $HR^1R^2C$—$CX^1F$—$(C=O)$—Y or of formula (V) $R^1R^2C=CF$—$(C=O)$—Y in which
  - $R^1$ and $R^2$ are independently selected from H, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl;
  - Y is selected from the group consisting of H, $C_1$-$C_{10}$-alkyl, $C_1$-$C_{10}$-haloalkyl, $C_6$-$C_{10}$-aryl, —OH, —OR, —NH$_2$, —NHR, —NR$_2$, —SR, $C_3$-$C_{10}$-cycloalkyl, $C_3$-$C_{10}$-cycloalkenyl and $C_2$-$C_{10}$-alkenyl;
  - R is independently selected from the group consisting of $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl;
  - $X^1$=Cl, Br or I; and
- a2) placing said compound of formula (IV) $HR^1R^2C$—$CX^1F$—$(C=O)$—Y or of formula (V) $R^1R^2C=CF$—$(C=O)$—Y obtained in step a1) in contact with hydrofluoric acid under conditions that are effective for forming a stream A comprising said compound of formula (I) $HR^1R^2C$—$CF_2$—$(C=O)$—Y in which
  - $R^1$ and $R^2$ are independently selected from H, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl;
  - Y is selected from the group consisting of H, $C_1$-$C_{10}$-alkyl, $C_1$-$C_{10}$-haloalkyl, $C_6$-$C_{10}$-aryl, —OH, —OR, —NH$_2$, —NHR, —NR$_2$, —SR, $C_3$-$C_{10}$-cycloalkyl, $C_3$-$C_{10}$-cycloalkenyl and $C_2$-$C_{10}$-alkenyl;
  - R is independently selected from the group consisting of $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl; and
- b) recovery of said stream A comprising said compound of formula (I).

Preferably, the present process comprises the steps of:
- a1) placing the compound of formula (II) $R^1R^2C=CX^1$—$(C=O)$—Y or of formula (III) $HR^1R^2C$—$CX^1X^2$—$(C=O)$—Y in contact with hydrofluoric acid under conditions that are effective for forming a compound of formula (IV) $HR^1R^2C$—$CX^1F$—$(C=O)$—Y or of formula (V) $R^1R^2C=CF$—$(C=O)$—Y in which
  - $R^1$ and $R^2$ are independently selected from H, $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl;
  - Y is selected from the group consisting of H, $C_1$-$C_{10}$-alkyl, $C_1$-$C_{10}$-haloalkyl, $C_6$-$C_{10}$-aryl, —OH, —OR, $C_3$-$C_{10}$-cycloalkyl, $C_3$-$C_{10}$-cycloalkenyl and $C_2$-$C_{10}$-alkenyl;
  - R is independently selected from the group consisting of $C_1$-$C_{10}$-alkyl and $C_6$-$C_{10}$-aryl;
  - $X^1$=Cl or Br; and
- a2) placing said compound of formula (IV) $HR^1R^2C$—$CX^1F$—$(C=O)$—Y or of formula (V) $R^1R^2C=CF$—$(C=O)$—Y obtained in step a1) in contact with hydrofluoric acid under conditions that are effective for forming a stream A comprising said compound of formula (I) $HR^1R^2C$—$CF_2$—$(C=O)$—Y in which
  - $R^1$ and $R^2$ are independently selected from H, $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl;
  - Y is selected from the group consisting of H, $C_1$-$C_{10}$-alkyl, $C_1$-$C_{10}$-haloalkyl, $C_6$-$C_{10}$-aryl, —OH, —OR, $C_3$-$C_{10}$-cycloalkyl, $C_3$-$C_{10}$-cycloalkenyl and $C_2$-$C_{10}$-alkenyl;
  - R is independently selected from the group consisting of $C_1$-$C_{10}$-alkyl and $C_6$-$C_{10}$-aryl; and
- b) recovery of said stream A comprising said compound of formula (I).

In particular, the present process comprises the steps of:
- a1) placing the compound of formula (II) $R^1R^2C=CX^1$—$(C=O)$—Y or of formula (III) $HR^1R^2C$—$CX^1X^2$—$(C=O)$—Y in contact with hydrofluoric acid under conditions that are effective for forming a compound of formula (IV) $HR^1R^2C$—$CX^1F$—$(C=O)$—Y or of formula (V) $R^1R^2C=CF$—$(C=O)$—Y in which
  - $R^1$ and $R^2$ are independently selected from H, $C_1$-$C_3$-alkyl, $C_6$-$C_8$-aryl and $C_2$-$C_6$-alkenyl, $C_3$-$C_6$-cycloalkenyl and $C_3$-$C_6$-cycloalkyl;
  - Y is selected from the group consisting of H, —OH and —OR;
  - R is independently selected from the group consisting of $C_1$-$C_6$-alkyl and $C_6$-$C_8$-aryl;
  - $X^1$=Cl; and
- a2) placing said compound of formula (IV) $HR^1R^2C$—$CX^1F$—$(C=O)$—Y or of formula (V) $R^1R^2C=CF$—$(C=O)$—Y obtained in step a1) in contact with hydrofluoric acid under conditions that are effective for forming a stream A comprising said compound of formula (I) $HR^1R^2C$—$CF_2$—$(C=O)$—Y in which
  - $R^1$ and $R^2$ are independently selected from H, $C_1$-$C_3$-alkyl, $C_6$-$C_8$-aryl and $C_2$-$C_6$-alkenyl, $C_3$-$C_6$-cycloalkenyl and $C_3$-$C_6$-cycloalkyl;
  - Y is selected from the group consisting of H, —OH and —OR;
  - R is independently selected from the group consisting of $C_1$-$C_6$-alkyl and $C_6$-$C_8$-aryl;
- b) recovery of said stream A comprising said compound of formula (I).

More particularly, the present process comprises the steps of:
- a1) placing the compound of formula (II) $R^1R^2C=CX^1$—$(C=O)$—Y or of formula (III) $HR^1R^2C$—$CX^1X^2$—

(C=O)—Y in contact with hydrofluoric acid under conditions that are effective for forming a compound of formula (IV) $HR^1R^2C$—$CX^1F$—(C=O)—Y or of formula (V) $R^1R^2C$=CF—(C=O)—Y in which $R^1$=H, $R^2$=H, Y=—OH or —OR with R=$C_1$-$C_3$-alkyl and $C_6$-aryl and $X^1$=Cl; and a2) placing said compound of formula (IV) $HR^1R^2C$—$CX^1F$—(C=O)—Y or of formula (V) $R^1R^2C$=CF—(C=O)—Y obtained in step a1) in contact with hydrofluoric acid under conditions that are effective for forming the stream A comprising said compound of formula (I) $HR^1R^2C$—$CF_2$—(C=O)—Y in which $R^1$=H, $R^2$=H, Y=—OH or —OR with R=$C_1$-$C_3$-alkyl and $C_6$-aryl; and b) recovery of said stream A comprising said compound of formula (I).

According to a preferred embodiment, the stream A comprising said compound (I) recovered in step b) is purified or separated under conditions that are effective for forming a composition B comprising a compound of formula (I) $HR^1R^2C$—$CF_2$—(C=O)—Y. Separations that may be mentioned include condensation, evaporation, decantation, absorption, washing and liquid-liquid extraction. Purifications that may be mentioned include distillation, for example extractive distillation, azeotropic distillation, membrane separation, adsorption on a solid and more particularly adsorption on molecular sieves, alumina or active charcoal and drying. Preferably, the drying may be performed on molecular sieves, in particular on 3 to 4 Å molecular sieves.

Composition B comprises said compound of formula (I) as described above.

Advantageously, composition B comprises less than 500 ppm of water by weight on the basis of the total weight of composition B, advantageously less than 400 ppm of water, preferably less than 300 ppm of water, in particular less than 200 ppm of water by weight on the basis of the total weight of composition B.

Advantageously, composition B comprises less than 500 ppm of hydrofluoric acid by weight on the basis of the total weight of composition B, advantageously less than 400 ppm of hydrofluoric acid, preferably less than 300 ppm of hydrofluoric acid, more preferentially less than 200 ppm of hydrofluoric acid, in particular less than 100 ppm of hydrofluoric acid by weight on the basis of the total weight of composition B.

Advantageously, composition B comprises less than 100 ppm of a hydrogen halide other than hydrofluoric acid, preferably hydrogen chloride, by weight on the basis of the total weight of composition B, advantageously less than 75 ppm of a hydrogen halide other than hydrofluoric acid, preferably hydrogen chloride, preferably less than 50 ppm of a hydrogen halide other than hydrofluoric acid, preferably hydrogen chloride, in particular less than 20 ppm of a hydrogen halide other than hydrofluoric acid, preferably hydrogen chloride, by weight on the basis of the total weight of composition B.

Advantageously, composition B comprises less than 5% by weight of a compound of formula (IV) $HR^1R^2C$—$CX^1F$—(C=O)—Y or of formula (V) $R^1R^2C$=CF—(C=O)—Y, preferably less than 3% by weight, more preferentially less than 1% by weight, in particular less than 0.1% by weight, more particularly less than 5000 ppm by weight, favorably less than 1000 ppm by weight of a compound of formula (IV) $HR^1R^2C$—$CX^1F$—(C=O)—Y or of formula (V) $R^1R^2C$=CF—(C=O)—Y on the basis of the total weight of composition B.

Said composition B may also comprise less than 1000 ppm by weight of a compound of formula (II) $R^1R^2C$=$CX^1$—(C=O)—Y or of formula (III) $HR^1R^2C$—$CX^1X^2$—(C=O)—Y as described above, advantageously less than 800 ppm by weight, preferably less than 500 ppm by weight, in particular less than 100 ppm by weight of a compound of formula (II) $R^1R^2C$=$CX^1$—(C=O)—Y or of formula (III) $HR^1R^2C$—$CX^1X^2$—(C=O)—Y as described above on the basis of the total weight of composition B.

Preferably, besides the compound of formula (I), composition B may comprise:

less than 5% by weight of a compound of formula (IV) $HR^1R^2C$—$CX^1F$—(C=O)—Y or of formula (V) $R^1R^2C$=CF—(C=O)—Y, preferably less than 3% by weight, more preferentially less than 1% by weight, in particular less than 0.1% by weight, more particularly less than 5000 ppm by weight, favorably less than 1000 ppm by weight of a compound of formula (IV) $HR^1R^2C$—$CX^1F$—(C=O)—Y or of formula (V) $R^1R^2C$=CF—(C=O)—Y on the basis of the total weight of composition B;

optionally or not less than 1000 ppm by weight of a compound of formula (II) $R^1R^2C$=$CX^1$—(C=O)—Y or of formula (III) $HR^1R^2C$—$CX^1X^2$—(C=O)—Y as described above, advantageously less than 800 ppm by weight, preferably less than 500 ppm by weight, in particular less than 100 ppm by weight of a compound of formula (II) $R^1R^2C$=$CX^1$—(C=O)—Y or of formula (III) $HR^1R^2C$—$CX^1X^2$—(C=O)—Y as described above; and optionally or not less than 500 ppm of water by weight, advantageously less than 400 ppm of water, preferably less than 300 ppm of water, in particular less than 200 ppm of water by weight; and optionally or not less than 500 ppm of hydrofluoric acid by weight, advantageously less than 400 ppm of hydrofluoric acid, preferably less than 300 ppm of hydrofluoric acid, more preferentially less than 200 ppm of hydrofluoric acid, in particular less than 100 ppm of hydrofluoric acid by weight; and optionally or not less than 100 ppm of a hydrogen halide other than hydrofluoric acid, preferably hydrogen chloride, advantageously less than 75 ppm of a hydrogen halide other than hydrofluoric acid, preferably hydrogen chloride, preferably less than 50 ppm of a hydrogen halide other than hydrofluoric acid, preferably hydrogen chloride, in particular less than 20 ppm of a hydrogen halide other than hydrofluoric acid, preferably hydrogen chloride, by weight on the basis of the total weight of composition B.

More preferentially, besides the compound of formula (I), composition B comprises:

less than 5% by weight of a compound of formula (IV) $HR^1R^2C$—$CX^1F$—(C=O)—Y or of formula (V) $R^1R^2C$=CF—(C=O)—Y, preferably less than 3% by weight, more preferentially less than 1% by weight, in particular less than 0.1% by weight, more particularly less than 5000 ppm by weight, favorably less than 1000 ppm by weight of a compound of formula (IV) $HR^1R^2C$—$CX^1F$—(C=O)—Y or of formula (V) $R^1R^2C$=CF—(C=O)—Y on the basis of the total weight of composition B;

less than 500 ppm of water by weight, advantageously less than 400 ppm of water, preferably less than 300 ppm of water, in particular less than 200 ppm of water by weight;

optionally or not less than 500 ppm of hydrofluoric acid by weight, advantageously less than 400 ppm of hydrofluoric acid, preferably less than 300 ppm of hydrofluoric acid, more preferentially less than 200 ppm of hydrofluoric acid, in particular less than 100 ppm of hydrofluoric acid by weight; and optionally or not less than 100 ppm of a hydrogen halide other than hydrofluoric acid, preferably hydrogen chloride, advantageously less than 75 ppm of a hydrogen halide other than hydrofluoric acid, preferably hydrogen chloride, preferably less than 50 ppm of a hydrogen halide other than hydrofluoric acid, preferably hydrogen chloride, in particular less than 20 ppm of a hydrogen halide other than hydrofluoric acid, preferably hydrogen chloride, optionally or not less than 1000 ppm by weight of a compound of formula (II) $R^1R^2C=CX^1-(C=O)-Y$ or of formula (III) $HR^1R^2C-CX^1X^2-(C=O)-Y$ as described above, advantageously less than 800 ppm by weight, preferably less than 500 ppm by weight, in particular less than 100 ppm by weight of a compound of formula (II) $R^1R^2C=CX^1-(C=O)-Y$ or of formula (III) $HR^1R^2C-CX^1X^2-(C=O)-Y$ as described above; and by weight on the basis of the total weight of composition B.

In particular, besides the compound of formula (I), composition B comprises:

less than 5% by weight of a compound of formula (IV) $HR^1R^2C-CX^1F-(C=O)-Y$ or of formula (V) $R^1R^2C=CF-(C=O)-Y$, preferably less than 3% by weight, more preferentially less than 1% by weight, in particular less than 0.1% by weight, more particularly less than 5000 ppm by weight, favorably less than 1000 ppm by weight of a compound of formula (IV) $HR^1R^2C-CX^1F-(C=O)-Y$ or of formula (V) $R^1R^2C=CF-(C=O)-Y$ on the basis of the total weight of composition B;

less than 500 ppm of water by weight, advantageously less than 400 ppm of water, preferably less than 300 ppm of water, in particular less than 200 ppm of water by weight;

less than 500 ppm of hydrofluoric acid by weight, advantageously less than 400 ppm of hydrofluoric acid, preferably less than 300 ppm of hydrofluoric acid, more preferentially less than 200 ppm of hydrofluoric acid, in particular less than 100 ppm of hydrofluoric acid by weight; and less than 100 ppm of a hydrogen halide other than hydrofluoric acid, preferably hydrogen chloride, advantageously less than 75 ppm of a hydrogen halide other than hydrofluoric acid, preferably hydrogen chloride, preferably less than 50 ppm of a hydrogen halide other than hydrofluoric acid, preferably hydrogen chloride, in particular less than 20 ppm of a hydrogen halide other than hydrofluoric acid, preferably hydrogen chloride, optionally less than 1000 ppm by weight of a compound of formula (II) $R^1R^2C=CX^1-(C=O)-Y$ or of formula (III) $HR^1R^2C-CX^1X^2-(C=O)-Y$ as described above, advantageously less than 800 ppm by weight, preferably less than 500 ppm by weight, in particular less than 100 ppm by weight of a compound of formula (II) $R^1R^2C=CX^1-(C=O)-Y$ or of formula (III) $HR^1R^2C-CX^1X^2-(C=O)-Y$ as described above; and by weight on the basis of the total weight of composition B.

According to a preferred embodiment, in the compounds of formula (I), (II), (III) and optionally (IV) and (V), Y is —OH; and the compound of formula (I) in which Y is —OH is treated under conditions that are effective for forming a compound of formula (I) in which Y is —OR, R being selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl.

Thus, the present process may comprise the steps of:
a) placing a compound of formula (II) $R^1R^2C=CX^1-(C=O)-Y$ or of formula (III) $HR^1R^2C-CX^1X^2-(C=O)-Y$ in contact with hydrofluoric acid; in which
$R^1$ and $R^2$ are independently selected from H, F, Cl, Br, I, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; advantageously, $R^1$ and $R^2$ are independently selected from H, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; preferably, $R^1$ and $R^2$ are independently selected from H, $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl; in particular, $R^1$ and $R^2$ are independently selected from H, $C_1$-$C_3$-alkyl, $C_6$-$C_8$-aryl and $C_2$-$C_6$-alkenyl, $C_3$-$C_6$-cycloalkenyl and $C_3$-$C_6$-cycloalkyl; more particularly, $R^1$ and $R^2$ are H;
$X^1$ and $X^2$ are independently selected from F, Cl, Br and I on condition that $X^1$ and $X^2$ are not simultaneously F; advantageously, $X^1$ and $X^2$ are F or Cl on condition that $X^1$ and $X^2$ are not simultaneously F; preferably, $X^1$ and $X^2$ are Cl;
Y is —OH; and
b) recovery of a stream A comprising said compound of formula (I) $HR^1R^2C-CF_2-(C=O)-Y$ in which Y is —OH and $R^1$ and $R^2$ are as defined in step a);
c) performing, starting with said stream A recovered in step b), an esterification reaction on the compound of formula (I) under conditions that are effective for forming a compound of formula (I) $HR^1R^2C-CF_2-(C=O)-Y$ in which Y is —OR with R being selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; advantageously, R being selected from the group consisting of $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl; preferably, R being selected from the group consisting of $C_1$-$C_{10}$-alkyl and $C_6$-$C_{10}$-aryl; in particular, R being selected from the group consisting of $C_1$-$C_6$-alkyl and $C_6$-$C_8$-aryl; more particularly, R being selected from the group consisting of $C_1$-$C_3$-alkyl and $C_6$-aryl; favorably, R being selected from the group consisting of $C_1$-$C_3$-alkyl.

Preferably, the group $R^1$ is identical in the compounds of formulae (II), (III) and (I). Preferably, the group $R^2$ is identical in the compounds of formulae (II), (III) and (I).

Preferably, the present process may comprise the steps of:
a) placing a compound of formula (II) $R^1R^2C=CX^1-(C=O)-Y$ or of formula (III) $HR^1R^2C-CX^1X^2-(C=O)-Y$ in contact with hydrofluoric acid to form a compound of formula (I) $HR^1R^2C-CF_2-(C=O)-Y$; in which
$R^1$ and $R^2$ are H;
$X^1$ and $X^2$ are Cl;
Y is —OH; and
b) recovery of a stream A comprising said compound of formula (I) $HR^1R^2C-CF_2-(C=O)-Y$ in which Y is —OH and $R^1$ and $R^2$ are as defined in step a);
c) performing, starting with said stream A recovered in step b), an esterification reaction on the compound of formula (I) under conditions that are effective for forming a compound of formula (I) $HR^1R^2C-CF_2-$ (C=O)—Y in which Y is —OR with R being $C_1$-$C_6$-alkyl; preferably, R is —$CH_3$, —$CH_2CH_3$ or —$CH_2CH_2CH_3$.

Preferably, step a) is performed under operating conditions as described above in connection with the process according to the present invention.

Preferably, step c) is performed by reacting the compound of formula (I) recovered in step b) with a compound of formula R—OH with R being selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; advantageously, R being selected from the group consisting of $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl; preferably, R being selected from the group consisting of $C_1$-$C_{10}$-alkyl and $C_6$-$C_{10}$-aryl; in particular, R being selected from the group consisting of $C_1$-$C_6$-alkyl and $C_6$-$C_8$-aryl; more particularly, R being selected from the group consisting of $C_1$-$C_3$-alkyl and $C_6$-aryl; favorably, R being selected from the group consisting of $C_1$-$C_3$-alkyl.

The process may be performed via steps a1) and a2) as described in the present patent application instead of step a). Thus, the present process may comprise the steps of:

a1) placing the compound of formula (II) $R^1R^2C=CX^1$—(C=O)—Y or of formula (III) $HR^1R^2C$—$CX^1X^2$—(C=O)—Y in contact with hydrofluoric acid under conditions that are effective for forming a compound of formula (IV) $HR^1R^2C$—$CX^1F$—(C=O)—Y or of formula (V) $R^1R^2C=CF$—(C=O)—Y with $R^1$, $R^2$, Y being as defined above and $X^1$ is Cl, Br and I; and a2) placing said compound of formula (IV) $HR^1R^2C$—$CX^1F$—(C=O)—Y or of formula (V) $R^1R^2C=CF$—(C=O)—Y obtained in step a1) in contact with hydrofluoric acid under conditions that are effective for forming a stream A comprising said compound of formula (I) $HR^1R^2C$—$CF_2$—(C=O)—Y;

b) recovery of a stream A comprising said compound of formula (I) $HR^1R^2C$—$CF_2$—(C=O)—Y in which Y is —OH and $R^1$ and $R^2$ are as defined in step a);

c) performing, starting with said stream A recovered in step b), an esterification reaction on the compound of formula (I) under conditions that are effective for forming a compound of formula (I) $HR^1R^2C$—$CF_2$—(C=O)—Y in which Y is —OR with R, $R^1$, $R^2$, $X^1$ and $X^2$ as defined above in relation with this preferred embodiment including step c).

Said stream A recovered in step b) may be purified as described in the present patent application to form said composition B prior to performing step c). Step c) is then performed starting with said composition B as defined in the present patent application.

Preferably, step c) is performed in the presence of an acid catalyst such as a Lewis acid or a Brnsted acid, or a basic catalyst or cationic or anionic resins. In particular, step c) is performed in the presence of a basic catalyst such as alkali metal or alkaline-earth metal hydroxides (for example KOH, NaOH, Ca(OH)$_2$, Mg(OH)$_2$), alkali metal or alkaline-earth metal oxides (for example Na$_2$O, CaO, MgO, K$_2$O), alkali metal or alkaline-earth metal carbonates (for example Na$_2$CO$_3$, K$_2$CO$_3$, CaCO$_3$, MgCO$_3$), or an acid catalyst such as a mineral acid (for example HCl, HBr, HI, H$_2$SO$_4$), p-toluenesulfonic acid, boron trifluoride.

Preferably, step c) may be performed at a temperature of between 10° C. and 200° C., advantageously between 20° C. and 150° C.

According to a second aspect, the present invention relates to a composition comprising said compound of formula (I) $HR^1R^2C$—$CF_2$—(C=O)—Y as described above.

Advantageously, the composition comprises less than 500 ppm of water by weight on the basis of the total weight of the composition, advantageously less than 400 ppm of water, preferably less than 300 ppm of water, in particular less than 200 ppm of water by weight on the basis of the total weight of the composition.

Advantageously, the composition comprises less than 500 ppm of hydrofluoric acid by weight on the basis of the total weight of the composition, advantageously less than 400 ppm of hydrofluoric acid, preferably less than 300 ppm of hydrofluoric acid, more preferentially less than 200 ppm of hydrofluoric acid, in particular less than 100 ppm of hydrofluoric acid by weight on the basis of the total weight of the composition.

Advantageously, the composition comprises less than 100 ppm of a hydrogen halide other than hydrofluoric acid, preferably hydrogen chloride, by weight on the basis of the total weight of the composition, advantageously less than 75 ppm of a hydrogen halide other than hydrofluoric acid, preferably hydrogen chloride, preferably less than 50 ppm of a hydrogen halide other than hydrofluoric acid, preferably hydrogen chloride, in particular less than 20 ppm of a hydrogen halide other than hydrofluoric acid, preferably hydrogen chloride, by weight on the basis of the total weight of the composition.

Advantageously, the composition comprises less than 5% by weight of a compound of formula (IV) $HR^1R^2C$—$CX^1F$—(C=O)—Y or of formula (V) $R^1R^2C=CF$—(C=O)—Y, preferably less than 3% by weight, more preferentially less than 1% by weight, in particular less than 0.1% by weight, more particularly less than 5000 ppm by weight, favorably less than 1000 ppm by weight of a compound of formula (IV) $HR^1R^2C$—$CX^1F$—(C=O)—Y or of formula (V) $R^1R^2C=CF$—(C=O)—Y on the basis of the total weight of the composition.

Said composition may also comprise less than 1000 ppm by weight of a compound of formula (II) $R^1R^2C=CX^1$—(C=O)—Y or of formula (III) $HR^1R^2C$—$CX^1X^2$—(C=O)—Y as described above, advantageously less than 800 ppm by weight, preferably less than 500 ppm by weight, in particular less than 100 ppm by weight of a compound of formula (II) $R^1R^2C=CX^1$—(C=O)—Y or of formula (III) $HR^1R^2C$—$CX^1X^2$—(C=O)—Y as described above on the basis of the total weight of the composition.

Preferably, besides the compound of formula (I), the composition may comprise:
less than 5% by weight of a compound of formula (IV) $HR^1R^2C$—$CX^1F$—(C=O)—Y or of formula (V) $R^1R^2C=CF$—(C=O)—Y, preferably less than 3% by weight, more preferentially less than 1% by weight, in particular less than 0.1% by weight, more particularly less than 5000 ppm by weight, favorably less than 1000 ppm by weight of a compound of formula (IV) $HR^1R^2C$—$CX^1F$—(C=O)—Y or of formula (V) $R^1R^2C=CF$—(C=O)—Y on the basis of the total weight of the composition;
optionally or not less than 1000 ppm by weight of a compound of formula (II) $R^1R^2C=CX^1$—(C=O)—Y or of formula (III) $HR^1R^2C$—$CX^1X^2$—(C=O)—Y as described above, advantageously less than 800 ppm by weight, preferably less than 500 ppm by weight, in particular less than 100 ppm by weight of a compound of formula (II) $R^1R^2C=CX^1—(C=O)—Y$ or of formula (III) $HR^1R^2C—CX^1X^2—(C=O)—Y$ as described above; and optionally or not less than 500 ppm of water by weight, advantageously less than 400 ppm of water, preferably less than 300 ppm of water, in particular less than 200 ppm of water by weight; and optionally or not less than 500 ppm of hydrofluoric acid by weight, advantageously less than 400 ppm of hydrofluoric acid, preferably less than 300 ppm of hydrofluoric acid, more preferentially less than 200 ppm of hydrofluoric acid, in particular less than 100 ppm of hydrofluoric acid by weight; and optionally or not less than 100 ppm of a hydrogen halide other than hydrofluoric acid, preferably hydrogen chloride, advantageously less than 75 ppm of a hydrogen halide other than hydrofluoric acid, preferably hydrogen chloride, preferably less than 50 ppm of a hydrogen halide other than hydrofluoric acid, preferably hydrogen chloride, in particular less than 20 ppm of a hydrogen halide other than hydrofluoric acid, preferably hydrogen chloride, by weight on the basis of the total weight of the composition.

More preferentially, besides the compound of formula (I), the composition comprises:

less than 5% by weight of a compound of formula (IV) $HR^1R^2C—CX^1F—(C=O)—Y$ or of formula (V) $R^1R^2C=CF—(C=O)—Y$, preferably less than 3% by weight, more preferentially less than 1% by weight, in particular less than 0.1% by weight, more particularly less than 5000 ppm by weight, favorably less than 1000 ppm by weight of a compound of formula (IV) $HR^1R^2C—CX^1F—(C=O)—Y$ or of formula (V) $R^1R^2C=CF—(C=O)—Y$ on the basis of the total weight of the composition;

less than 500 ppm of water by weight, advantageously less than 400 ppm of water, preferably less than 300 ppm of water, in particular less than 200 ppm of water by weight;

optionally or not less than 500 ppm of hydrofluoric acid by weight, advantageously less than 400 ppm of hydrofluoric acid, preferably less than 300 ppm of hydrofluoric acid, more preferentially less than 200 ppm of hydrofluoric acid, in particular less than 100 ppm of hydrofluoric acid by weight; and optionally or not less than 100 ppm of a hydrogen halide other than hydrofluoric acid, preferably hydrogen chloride, advantageously less than 75 ppm of a hydrogen halide other than hydrofluoric acid, preferably hydrogen chloride, preferably less than 50 ppm of a hydrogen halide other than hydrofluoric acid, preferably hydrogen chloride, in particular less than 20 ppm of a hydrogen halide other than hydrofluoric acid, preferably hydrogen chloride, optionally or not less than 1000 ppm by weight of a compound of formula (II) $R^1R^2C=CX^1—(C=O)—Y$ or of formula (III) $HR^1R^2C—CX^1X^2—(C=O)—Y$ as described above, advantageously less than 800 ppm by weight, preferably less than 500 ppm by weight, in particular less than 100 ppm by weight of a compound of formula (II) $R^1R^2C=CX^1—(C=O)—Y$ or of formula (III) $HR^1R^2C—CX^1X^2—(C=O)—Y$ as described above; and by weight on the basis of the total weight of the composition.

In particular, besides the compound of formula (I), the composition comprises:

less than 5% by weight of a compound of formula (IV) $HR^1R^2C—CX^1F—(C=O)—Y$ or of formula (V) $R^1R^2C=CF—(C=O)—Y$, preferably less than 3% by weight, more preferentially less than 1% by weight, in particular less than 0.1% by weight, more particularly less than 5000 ppm by weight, favorably less than 1000 ppm by weight of a compound of formula (IV) $HR^1R^2C—CX^1F—(C=O)—Y$ or of formula (V) $R^1R^2C=CF—(C=O)—Y$ on the basis of the total weight of the composition;

less than 500 ppm of water by weight, advantageously less than 400 ppm of water, preferably less than 300 ppm of water, in particular less than 200 ppm of water by weight;

less than 500 ppm of hydrofluoric acid by weight, advantageously less than 400 ppm of hydrofluoric acid, preferably less than 300 ppm of hydrofluoric acid, more preferentially less than 200 ppm of hydrofluoric acid, in particular less than 100 ppm of hydrofluoric acid by weight; and less than 100 ppm of a hydrogen halide other than hydrofluoric acid, preferably hydrogen chloride, advantageously less than 75 ppm of a hydrogen halide other than hydrofluoric acid, preferably hydrogen chloride, preferably less than 50 ppm of a hydrogen halide other than hydrofluoric acid, preferably hydrogen chloride, in particular less than 20 ppm of a hydrogen halide other than hydrofluoric acid, preferably hydrogen chloride, optionally less than 1000 ppm by weight of a compound of formula (II) $R^1R^2C=CX^1—(C=O)—Y$ or of formula (III) $HR^1R^2C—CX^1X^2—(C=O)—Y$ as described above, advantageously less than 800 ppm by weight, preferably less than 500 ppm by weight, in particular less than 100 ppm by weight of a compound of formula (II) $R^1R^2C=CX^1—(C=O)—Y$ or of formula (III) $HR^1R^2C—CX^1X^2—(C=O)—Y$ as described above; and by weight on the basis of the total weight of the composition.

Advantageously, said composition according to this second aspect of the invention is obtained via the process according to the first aspect of the present invention.

Advantageously, in said composition, the compounds of formula (I), (II), (III), (IV) and/or (V) are such that:

$R^1$ and $R^2$ are independently selected from H, F, Cl, Br, I, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl;

$X^1$ and $X^2$ are independently selected from F, Cl, Br and I on condition that $X^1$ and $X^2$ are not simultaneously F;

Y is selected from the group consisting of H, $C_1$-$C_{20}$-alkyl, $C_1$-$C_{20}$-haloalkyl, $C_6$-$C_{20}$-aryl, —OH, —OR, —NH$_2$, —NHR, —NR$_2$, —SR, $C_3$-$C_{20}$-cycloalkyl, $C_3$-$C_{20}$-cycloalkenyl and $C_2$-$C_{20}$-alkenyl;

R is independently selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl.

Preferably, in said composition, the compounds of formula (I), (II), (III), (IV) and/or (V) are such that $R^1$ and $R^2$ are independently selected from H, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl. In particular, in said composition, the compounds of formula (I), (II), (III), (IV) and/or (V) are such that $R^1$ and $R^2$ are independently selected from H, $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl. Favorably, in said composition, the compounds of formula (I), (II), (III), (IV) and/or (V) are such that $R^1$ and $R^2$ are independently selected from H, $C_1$-$C_3$-alkyl, $C_6$-$C_8$-aryl and $C_2$-$C_6$-alkenyl, $C_3$-$C_6$-cycloalkenyl and $C_3$-$C_6$-cycloalkyl. Particularly favorably, in said composition, the compounds of formula (I), (II), (III), (IV) and/or (V) are such that $R^1$ and $R^2$ are H.

Preferably, in said composition, the compounds of formula (I), (II), (III), (IV) and/or (V) are such that $X^1$ and $X^2$ are independently selected from F, Cl and Br on condition that $X^1$ and $X^2$ are not simultaneously F. More preferentially, in said composition, the compounds of formula (I), (II), (III), (IV) and/or (V) are such that $X^1$ and $X^2$ are independently selected from F and Cl on condition that $X^1$ and $X^2$ are not simultaneously F. In particular, in said composition, the compounds of formula (I), (II), (III), (IV) and/or (V) are such that $X^1$ and $X^2$ are Cl.

Preferably, in said composition, the compounds of formula (I), (II), (III), (IV) and/or (V) are such that Y is selected from the group consisting of H, $C_1$-$C_{10}$-alkyl, $C_1$-$C_{10}$-haloalkyl, $C_6$-$C_{10}$-aryl, —OH, —OR, —NH$_2$, —NHR, —NR$_2$, —SR, $C_3$-$C_{10}$-cycloalkyl, $C_3$-$C_{10}$-cycloalkenyl and $C_2$-$C_{10}$-alkenyl. More preferentially, in said composition, the compounds of formula (I), (II), (III), (IV) and/or (V) are such that Y is selected from the group consisting of H, $C_1$-$C_{10}$-alkyl, $C_1$-$C_{10}$-haloalkyl, $C_6$-$C_{10}$-aryl, —OH, —OR, $C_3$-$C_{10}$-cycloalkyl, $C_3$-$C_{10}$-cycloalkenyl and $C_2$-$C_{10}$-alkenyl. In particular, in said composition, the compounds of formula (I), (II), (III), (IV) and/or (V) are such that Y is selected from the group consisting of H, —OH and —OR. More particularly, in said composition, the compounds of formula (I), (II), (III), (IV) and/or (V) are such that Y is selected from the group consisting of —OH and —OR.

Preferably, R is independently selected from the group consisting of $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl. In particular, R is independently selected from the group consisting of $C_1$-$C_{10}$-alkyl and $C_6$-$C_{10}$-aryl. More particularly, R is independently selected from the group consisting of $C_1$-$C_6$-alkyl and $C_6$-$C_8$-aryl. Favorably, R is independently selected from the group consisting of $C_1$-$C_3$-alkyl and $C_6$-aryl.

Thus, the present composition comprises a compound of formula (I) $HR^1R^2C$—$CF_2$—$(C=O)$—Y in which
  $R^1$ and $R^2$ are independently selected from H, F, Cl, Br, I, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; preferably selected from H, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; in particular selected from H, $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl; favorably selected from H, $C_1$-$C_3$-alkyl, $C_6$-$C_8$-aryl and $C_2$-$C_6$-alkenyl, $C_3$-$C_6$-cycloalkenyl and $C_3$-$C_6$-cycloalkyl; particularly favorably, $R^1$ and $R^2$ are H;
  Y is selected from the group consisting of H, $C_1$-$C_{20}$-alkyl, $C_1$-$C_{20}$-haloalkyl, $C_6$-$C_{20}$-aryl, —OH, —OR, —NH$_2$, —NHR, —NR$_2$, —SR, $C_3$-$C_{20}$-cycloalkyl, $C_3$-$C_{20}$-cycloalkenyl and $C_2$-$C_{20}$-alkenyl; preferably selected from the group consisting of H, $C_1$-$C_{10}$-alkyl, $C_1$-$C_{10}$-haloalkyl, $C_6$-$C_{10}$-aryl, —OH, —OR, —NH$_2$, —NHR, —NR$_2$, —SR, $C_3$-$C_{10}$-cycloalkyl, $C_3$-$C_{10}$-cycloalkenyl and $C_2$-$C_{10}$-alkenyl; more preferentially selected from the group consisting of H, $C_1$-$C_{10}$-alkyl, $C_1$-$C_{10}$-haloalkyl, $C_6$-$C_{10}$-aryl, —OH, —OR, $C_3$-$C_{10}$-cycloalkyl, $C_3$-$C_{10}$-cycloalkenyl and $C_2$-$C_{10}$-alkenyl; in particular selected from the group consisting of H, —OH and —OR; more particularly, Y is selected from the group consisting of —OH and —OR;
  R is independently selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; preferably selected from the group consisting of $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl; in particular selected from the group consisting of $C_1$-$C_{10}$-alkyl and $C_6$-$C_{10}$-aryl; more particularly selected from the group consisting of $C_1$-$C_6$-alkyl and $C_6$-$C_8$-aryl; favorably, R is independently selected from the group consisting of $C_1$-$C_3$-alkyl and $C_6$-aryl.

If said composition comprises compounds of formula (II), (111), (IV) and/or (V), they are such that:
  $X^1$ and $X^2$ are independently selected from F, Cl, Br and I on condition that $X^1$ and $X^2$ are not simultaneously F; preferably selected from F, Cl and Br on condition that $X^1$ and $X^2$ are not simultaneously F; more preferentially selected from F and Cl on condition that $X^1$ and $X^2$ are not simultaneously F; in particular, $X^1$ and $X^2$ are Cl;
  $R^1$ and $R^2$ are independently selected from H, F, Cl, Br, I, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; preferably selected from H, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; in particular selected from H, $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl; favorably selected from H, $C_1$-$C_3$-alkyl, $C_6$-$C_8$-aryl and $C_2$-$C_6$-alkenyl, $C_3$-$C_6$-cycloalkenyl and $C_3$-$C_6$-cycloalkyl; particularly favorably, $R^1$ and $R^2$ are H;
  Y is selected from the group consisting of H, $C_1$-$C_{20}$-alkyl, $C_1$-$C_{20}$-haloalkyl, $C_6$-$C_{20}$-aryl, —OH, —OR, —NH$_2$, —NHR, —NR$_2$, —SR, $C_3$-$C_{20}$-cycloalkyl, $C_3$-$C_{20}$-cycloalkenyl and $C_2$-$C_{20}$-alkenyl; preferably selected from the group consisting of H, $C_1$-$C_{10}$-alkyl, $C_1$-$C_{10}$-haloalkyl, $C_6$-$C_{10}$-aryl, —OH, —OR, —NH$_2$, —NHR, —NR$_2$, —SR, $C_3$-$C_{10}$-cycloalkyl, $C_3$-$C_{10}$-cycloalkenyl and $C_2$-$C_{10}$-alkenyl; more preferentially selected from the group consisting of H, $C_1$-$C_{10}$-alkyl, $C_1$-$C_{10}$-haloalkyl, $C_6$-$C_{10}$-aryl, —OH, —OR, $C_3$-$C_{10}$-cycloalkyl, $C_3$-$C_{10}$-cycloalkenyl and $C_2$-$C_{10}$-alkenyl; in particular selected from the group consisting of H, —OH and —OR; more particularly, Y is selected from the group consisting of —OH and —OR;
  R is independently selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; preferably selected from the group consisting of $C_1$-$C_{10}$-alkyl, $C_6$-$C_{10}$-aryl and $C_2$-$C_{10}$-alkenyl, $C_3$-$C_{10}$-cycloalkenyl and $C_3$-$C_{10}$-cycloalkyl; in particular selected from the group consisting of $C_1$-$C_{10}$-alkyl and $C_6$-$C_{10}$-aryl; more particularly selected from the group consisting of $C_1$-$C_6$-alkyl and $C_6$-$C_8$-aryl; favorably, R is independently selected from the group consisting of $C_1$-$C_3$-alkyl and $C_6$-aryl.

In particular, the composition comprises a compound of formula (I) $HR^1R^2C$—$CF_2$—$(C=O)$—Y in which $R^1$ and $R^2$ are H; Y being selected from the group consisting of —OH and —OR; R being independently selected from the group consisting of $C_1$-$C_3$-alkyl and $C_6$-aryl. Said composition may also comprise compounds of formula (II), (III), (IV) and/or (V) such that $R^1$ and $R^2$ are H; Y being selected from the group consisting of —OH and —OR; R being independently selected from the group consisting of $C_1$-$C_3$-alkyl and $C_6$-aryl; and $X^1$ and $X^2$ being Cl.

The composition according to the second aspect of the present invention may be obtained according to the process described according to the first aspect of the invention.

According to a third aspect of the present invention, the composition according to the second aspect of the present invention is used as solvent in an electrolytic composition. The electrolytic composition is preferably used in a battery. In particular, the electrolytic composition is used in an Li-ion battery. According to a preferred embodiment, the electrolytic composition comprises, besides the present composition used as solvent, at least one lithium salt. Preferably, said at least one lithium salt is selected from the group consisting of $LiPF_6$, $LiBF_4$, $CH_3COOLi$, $CH_3SO_3Li$, $CF_3SO_3Li$, $CF_3COOLi$, $Li_2B_{12}F_{12}$, $LiBC_4O_8$, $LiAsF_6$, $Li_2SiF_6$, $Li_2PFO_3$, $LiClO_4$, lithium bis(trifluoromethanesulfonyl)imide, lithium bis(fluorosulfonyl)imide, lithium 2-trifluoromethyl-4,5-dicyanoimidazolate, lithium 2-pentafluoroethyl-4,5-dicyanoimidazolate.

The composition according to the second aspect of the present invention may also be used as additive in an electrolytic composition. The electrolytic composition is preferably used in a battery. In particular, the electrolytic composition is used in an Li-ion battery. According to a preferred embodiment, the electrolytic composition comprises, besides the present composition used as solvent, at least one lithium salt. Preferably, said at least one lithium salt is selected from the group consisting of $LiPF_6$, $LiBF_4$, $CH_3COOLi$, $CH_3SO_3Li$, $CF_3SO_3Li$, $CF_3COOLi$, $Li_2B_{12}F_{12}$, $LiBC_4O_8$, $LiAsF_6$, $Li_2SiF_6$, $Li_2PFO_3$, $LiClO_4$, lithium bis(trifluoromethanesulfonyl)imide, lithium bis(fluorosulfonyl)imide, lithium 2-trifluoromethyl-4,5-dicyanoimidazolate, lithium 2-pentafluoroethyl-4,5-dicyanoimidazolate.

EXAMPLES

Example 1—Synthesis of 2,2-difluoropropionic acid

The equipment used is composed of a 316L stainless-steel autoclave with a volume of 0.8 L, on which is mounted a condenser and a pressure-regulating valve. The autoclave is immersed in liquid nitrogen and the following constituents are successively introduced: 140 g (7.0 mol) of hydrofluoric acid, 100 g (0.7 mol) of 2,2-dichloropropionic acid and 13.3 g (0.07 mol) of titanium tetrachloride ($TiCl_4$). The temperature of the autoclave is then raised to room temperature (25° C.). The autoclave is then immersed in an oil bath and the temperature is raised to 125° C. while the temperature of the condenser is maintained at about 17° C. The pressure is set at 20 bara. During the reaction, the volatile products are removed continuously, washed in a water washer and collected. After 15 hours of reaction, the autoclave is cooled to room temperature. It is then degassed and the reaction products are washed, dried and analyzed by gas chromatography.

The yield of 2,2-difluoropropionic acid, expressed by the ratio of the number of moles of 2,2-difluoropropionic acid detected to the number of moles of 2,2-dichloropropionic acid initially introduced, is 77.6%. After distillation and drying, the purity of the 2,2-difluoropropionic acid is greater than 99%. The weight content of ethyl 2-chloro-2-fluoropropionate is 320 ppm, the weight content of HF is 23 ppm, the weight content of water is 52 ppm and the weight content of HCl is 5 ppm.

Example 2—Synthesis of ethyl 2,2-difluoropropionate $CH_3CF_2CO_2CH_2CH_3$

The equipment used is similar to that described in Example 1. The autoclave is immersed in liquid nitrogen and the following constituents are successively introduced: 140 g (7.0 mol) of hydrofluoric acid, 100 g (0.58 mol) of ethyl 2,2-dichloropropionate ($CH_3CCl_2CO_2CH_2CH_3$) and 18.2 g (0.07 mol) of tin tetrachloride $SnCl_4$. The autoclave is then immersed in an oil bath and the temperature is raised to 125° C. while the temperature of the condenser is maintained at about 17° C. The pressure is set at 20 bara. During the reaction, the volatile products are removed continuously, washed in a water washer and collected. After 15 hours of reaction, the autoclave is cooled to room temperature. It is then degassed and the reaction products are washed, dried and analyzed by gas chromatography.

The yield of ethyl 2,2-difluoropropionate, expressed by the ratio of the number of moles of ethyl 2,2-difluoropropionate detected to the number of moles of ethyl 2,2-dichloropropionate initially introduced, is 62.9%. After distillation and drying, the purity of the ethyl 2,2-difluoropropionate is greater than 99%. The weight content of ethyl 2-chloro-2-fluoropropionate is 287 ppm, the weight content of HF is 17 ppm, the weight content of water is 43 ppm and the weight content of HCl is 4 ppm.

Example 3—Synthesis of ethyl 2,2-difluoropropionate CH3CF2CO2CH2CH3

The equipment used is composed of a jacketed reactor with a volume of 2.0 L equipped with a mechanical stirrer and a device for measuring the temperature, and on which is mounted a distillation column with a reflux head and condenser allowing azeotropic distillation. The following are successively introduced into the reactor, which has been dried and flushed with nitrogen beforehand: 220 g (2.0 mol) of 2,2-difluoropropionic acid, 2 g (0.02 mol) of sulfuric acid, 600 ml of cyclohexene and 369 g (8.0 mol) of ethanol. The reaction is performed at atmospheric pressure, by feeding the jacket with a coolant fluid at a temperature of 80° C. After 6 hours of reaction, the excess acid is neutralized and the cyclohexane and the excess ethanol are removed under reduced pressure (P=200 mbar). The reaction products are dried and analyzed by gas chromatography. The yield of ethyl 2,2-difluoropropionate, expressed by the ratio of the number of moles of ethyl 2,2-difluoropropionate detected to the number of moles of 2,2-difluoropropionic acid initially introduced, is 91.6%. After distillation, the purity of the ethyl 2,2-difluoropropionate is greater than 98.3%.

The invention claimed is:

1. A process for preparing a compound of formula (I) $HR^1R^2C-CF_2-(C=O)-Y$, the process being carried out at a temperature of at least 30° C. and comprising the steps of:
   a) placing a compound of formula (II) $R^1R^2C=CX^1-(C=O)-Y$ or of formula (III) $HR^1R^2C-CX^1X^2-(C=O)-Y$ in contact with hydrofluoric acid;
   $R^1$ and $R^2$ being independently selected from H, F, Cl, Br, I, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl;
   $X^1$ and $X^2$ being independently selected from F, Cl, Br and I on condition that $X^1$ and $X^2$ are not simultaneously F;
   Y being selected from the group consisting of H, $C_1$-$C_{20}$-alkyl, $C_1$-$C_{20}$-haloalkyl, $C_6$-$C_{20}$-aryl, —OH, —OR, —$NH_2$, —NHR, —$NR_2$, —SR, $C_3$-$C_{20}$-cycloalkyl, $C_3$-$C_{20}$-cycloalkenyl and $C_2$-$C_{20}$-alkenyl;
   R being independently selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; and
   b) recovery of a stream A comprising said compound (1).
2. The process as claimed in claim 1, wherein Y is —OH or —OR.
3. The process as claimed in claim 1, wherein $R^1$ is H and $R^2$ is H.

4. The process as claimed in claim 1, wherein it is performed in the presence of a catalyst.

5. The process as claimed in claim 1, wherein it comprises the steps of:
- a1) placing the compound of formula (II) $R^1R^2C=CX^1-(C=O)-Y$ or of formula (III) $HR^1R^2C-CX^1X^2-(C=O)-Y$ in contact with hydrofluoric acid under conditions that are effective for forming a compound of formula (IV) $HR^1R^2C-CX^1F-(C=O)-Y$ or of formula (V) $R^1R^2C=CF-(C=O)-Y$ with $R^1$, $R^2$, Y being as defined in claim 1 and $X^1$ is Cl, Br and I; and
- a2) placing said compound of formula (IV) $HR^1R^2C-CX^1F-(C=O)-Y$ or of formula (V) $R^1R^2C=CF-(C=O)-Y$ obtained in step a1) in contact with hydrofluoric acid under conditions that are effective for forming said stream A comprising said compound of formula (I) $HR^1R^2C-CF_2-(C=O)-Y$; and
- b) recovery of said stream A comprising said compound (I).

6. The process as claimed in claim 5, wherein composition A obtained in step a2) comprises less than 15% by weight of compound of formula (IV) $HR^1R^2C-CX^1F-(C=O)-Y$ or of formula (V) $R^1R^2C=CF-(C=O)-Y$ on the basis of the total weight of the compounds of formula (I), (IV) or (IV).

7. The process as claimed in claim 5, wherein said stream A recovered in step b) is purified under conditions that are effective for forming a composition B comprising a compound of formula (I) $HR^1R^2C-CF_2-(C=O)-Y$, less than 1000 ppm of a compound of formula (IV) $HR^1R^2C-CX^1F-(C=O)-Y$ or of formula (V) $R^1R^2C=CF-(C=O)-Y$ and optionally less than 500 ppm of water and optionally less than 500 ppm of hydrofluoric acid and optionally less than 100 ppm of a hydrogen halide other than hydrofluoric acid.

8. The process as claimed in claim 1, wherein, in the compounds of formula (I), (II), (III) and optionally (IV) and (V), Y is —OH; and the compound of formula (I) in which Y is —OH is treated under conditions that are effective for forming a compound of formula (I) in which Y is —OR, R being selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl.

9. The process as claimed in claim 8, wherein R is a $C_1$-$C_6$-alkyl.

10. A composition comprising a compound of formula (V) $R^1R^2C=CF-(C=O)-Y$ and optionally or not less than 500 ppm of water and optionally or not less than 500 ppm of hydrofluoric acid and optionally or not less than 100 ppm of a hydrogen halide other than hydrofluoric acid; with $R^1$ and $R^2$ being independently selected from H, F, Cl, Br, I, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl;

$X^1$ being selected from Cl, Br and I;

Y being selected from the group consisting of H, $C_1$-$C_{20}$-alkyl, $C_1$-$C_{20}$-haloalkyl, $C_6$-$C_{20}$-aryl, —OH, —$NH_2$, —NHR, —$NR_2$, —SR, $C_3$-$C_{20}$-cycloalkyl, $C_3$-$C_{20}$-cycloalkenyl and $C_2$-$C_{20}$-alkenyl;

R being independently selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl.

11. A battery comprising the composition as claimed in claim 10 as a solvent in an electrolytic composition in the battery.

12. A process for preparing a compound of formula (I) $HR^1R^2C-CF_2-(C=O)-Y$ comprising the steps of:
- a) placing a compound of formula (II) $R^1R^2C=CX^1-(C=O)-Y$ or of formula (III) $HR^1R^2C-CX^1X^2-(C=O)-Y$ in contact with only hydrofluoric acid and optionally a metal catalyst and/or a solvent;

$R^1$ and $R^2$ being independently selected from H, F, Cl, Br, I, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl;

$X^1$ and $X^2$ being independently selected from F, Cl, Br and I on condition that $X^1$ and $X^2$ are not simultaneously F;

Y being selected from the group consisting of H, $C_1$-$C_{20}$-alkyl, $C_1$-$C_{20}$-haloalkyl, $C_6$-$C_{20}$-aryl, —OH, —OR, —$NH_2$, —NHR, —$NR_2$, —SR, $C_3$-$C_{20}$-cycloalkyl, $C_3$-$C_{20}$-cycloalkenyl and $C_2$-$C_{20}$-alkenyl;

R being independently selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; and

- b) recovery of a stream A comprising said compound (1).

13. A process comprising the steps of:
- a) placing the compound of formula (II) $R^1R^2C=CX^1-(C=O)-Y$ in contact with hydrofluoric acid under conditions that are effective for forming a compound of formula (V) $R^1R^2C=CF-(C=O)-Y$ with:

$R^1$ and $R^2$ being independently selected from H, F, Cl, Br, I, $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl;

$X^1$ being selected from Cl, Br and I;

Y being selected from the group consisting of H, $C_1$-$C_{20}$-alkyl, $C_1$-$C_{20}$-haloalkyl, $C_6$-$C_{20}$-aryl, —OH, —OR, —$NH_2$, —NHR, —$NR_2$, —SR, $C_3$-$C_{20}$-cycloalkyl, $C_3$-$C_{20}$-cycloalkenyl and $C_2$-$C_{20}$-alkenyl;

R being independently selected from the group consisting of $C_1$-$C_{20}$-alkyl, $C_6$-$C_{20}$-aryl and $C_2$-$C_{20}$-alkenyl, $C_3$-$C_{20}$-cycloalkenyl and $C_3$-$C_{20}$-cycloalkyl; and

- b) recovery of a stream A comprising said compound (1).

* * * * *